United States Patent [19]
Jones et al.

[11] Patent Number: 4,991,591
[45] Date of Patent: Feb. 12, 1991

[54] SPIROMETER WITH MULTI-STAGE FIXED ORIFICE

[76] Inventors: William C. Jones; William C. Jones, Jr., both of 200 Windsor Dr., Oak Brook, Ill. 60521

[21] Appl. No.: 369,744

[22] Filed: Jun. 22, 1989

[51] Int. Cl.$^5$ ............................................. A61B 5/08
[52] U.S. Cl. ..................................... 128/719; 128/725
[58] Field of Search ........ 128/716, 719, 720, 725–729, 128/72 M; 272/99; 73/49.8, 272 R, 861.52–861.58, 208, 253–255, 480; 137/14

[56] References Cited

U.S. PATENT DOCUMENTS

| | | | |
|---|---|---|---|
| 3,086,515 | 4/1963 | Jones | 128/2.08 |
| 3,321,976 | 5/1967 | Jones | 73/421.5 |
| 3,512,521 | 5/1970 | Jones | 128/2.08 |
| 3,527,206 | 9/1970 | Jones | 128/2.08 |
| 3,533,398 | 10/1970 | Jones | 128/2 |
| 3,589,190 | 6/1971 | Jones | 73/279 |
| 3,771,512 | 11/1973 | Jones et al. | 128/2.08 |
| 3,977,394 | 8/1976 | Jones et al. | 128/2.07 |
| 3,993,050 | 11/1976 | Robinson et al. | 128/2.08 |
| 4,250,890 | 2/1981 | Jones et al. | 128/728 |
| 4,259,967 | 4/1981 | Vooren et al. | 128/720 |
| 4,296,758 | 12/1981 | Garbe | 128/728 |
| 4,307,729 | 12/1981 | Hart et al. | 128/727 |
| 4,333,476 | 6/1982 | Downing, Jr. | 128/720 |
| 4,558,710 | 12/1985 | Eichler | 128/720 |
| 4,706,685 | 11/1987 | Jones, Jr. et al. | 128/725 |
| 4,841,982 | 6/1989 | Nikiforov et al. | 128/716 |
| 4,852,583 | 8/1989 | Walker | 128/716 |

*Primary Examiner*—David J. Isabella
*Assistant Examiner*—K. M. Reichle
*Attorney, Agent, or Firm*—Tilton, Fallon, Lungmus & Chestnut

[57] ABSTRACT

A spirometer for measuring breathing functions of a human subject includes a housing and a hollow elongate body with a first opening through which the subject inhales or exhales, a second opening through which the breath enters the elongate body when the subject inhales or discharges from the body when the subject exhales, and a third opening disposed between said first and second openings. The spirometer also includes a pressure transducer in fluid communication with the third opening of the elongate body. This transducer measures the pressure of the breath moving through the elongate body. A plug member disposed proximate the second opening of the elongate body closes a predetermined portion of the second opening when the rate of flow of the breath through the elongate body reaches a predetermined level.

8 Claims, 2 Drawing Sheets

FIG. 1
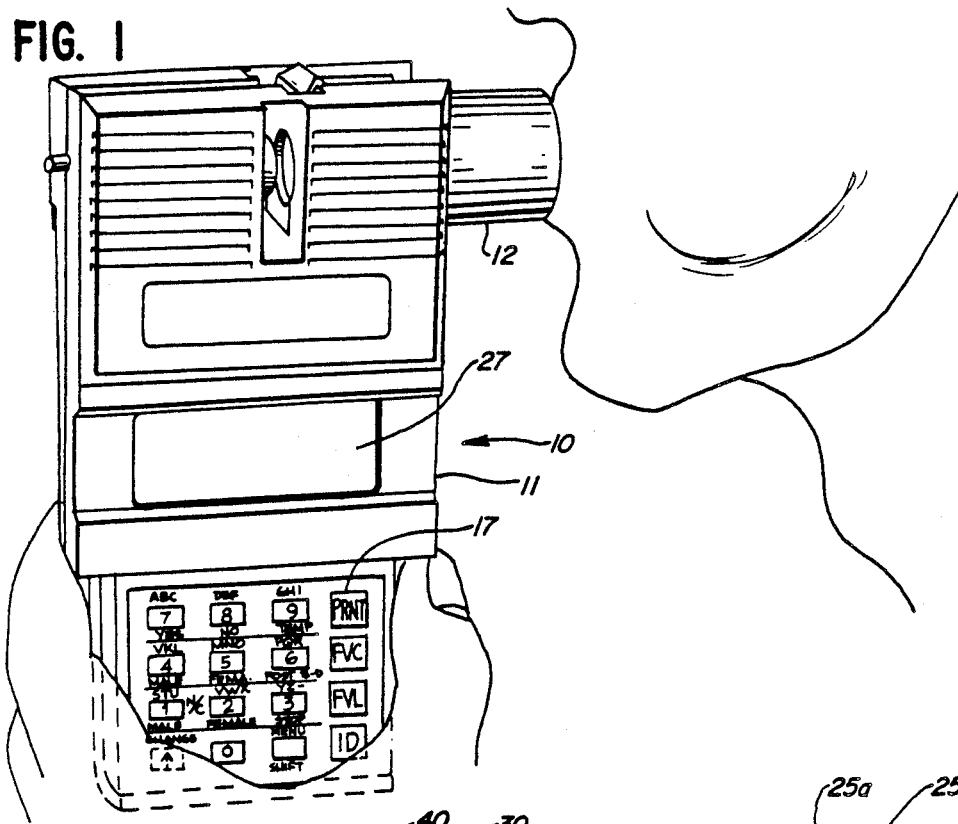
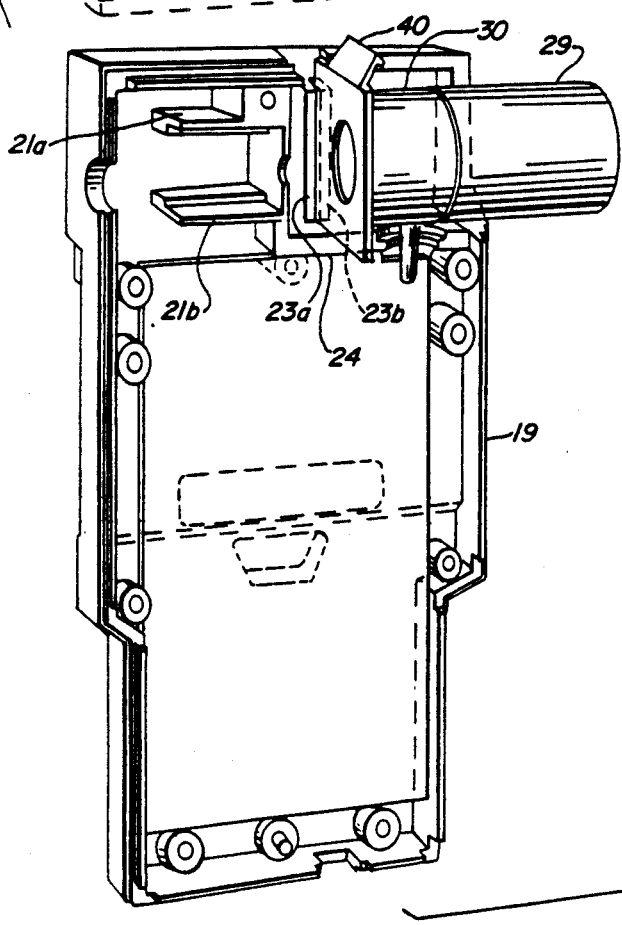
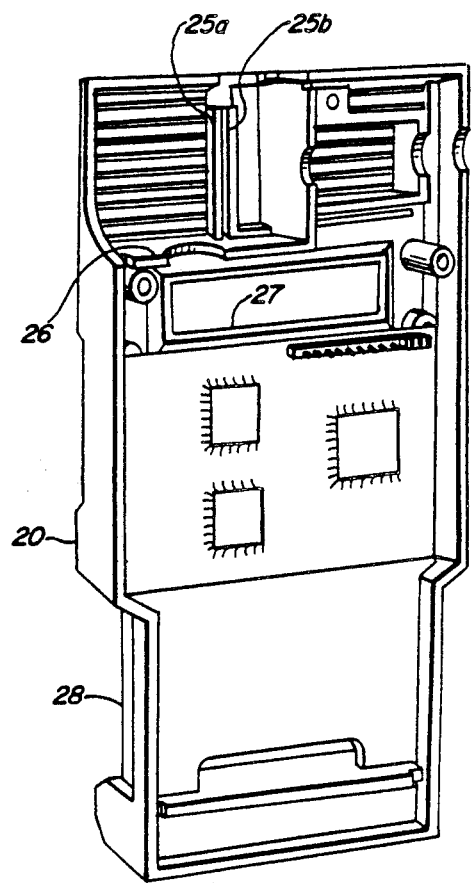
FIG. 2

SPIROMETER WITH MULTI-STAGE FIXED ORIFICE

BACKGROUND OF INVENTION

1. Field Of The Invention

The present invention relates generally to a spirometer. Specifically, this invention relates to a spirometer which measures the breathing volume or breathing rate of human subjects by sensing the back pressure developed in an open chamber through which the subject breathes. The chamber has an opening which varies in size so that the spirometer may provide accurate pressure readings over a wide range of flow rates.

2. Description Of The Prior Art

Spirometers measure the breathing volume or breathing rate of human subjects. For many applications, these devices require a simple construction to minimize malfunctions. They should also have a portable construction to allow a user to test human subjects at any one of a wide variety of locations, e.g. various industrial environments or at the bedside of a hospitalized patient. Moreover, they should provide precise, uniform and reliable performance.

Many prior art spirometers include a closed but distensible chamber into which a subject exhales or from which the subject inhales. The chamber expands or contracts in response to the force provided by the breath; and the spirometer measures the change in volume of the chamber. These prior spirometers are bulky and have a multiplicity of close tolerance components which make them susceptible to malfunctions and breakdowns. They also do not include any means for avoiding rebreathing cross-contamination Finally, producing these prior art spirometers requires accurate and expensive machines and machining techniques, complicated and time-consuming assembly processes, and the use of costly materials.

Other prior spirometers have open chambers; and they measure the back pressure of the breath which moves through the open chamber. Screens, grids, or filter papers placed over the opening through which breath moves in and out of this chamber constrict the flow of breath. Typically, this opening has a fixed diameter which does not allow the apparatus to measure pressures over a wide range of flow rates.

Still other prior spirometers have housings which define a chamber with an opening and which include a flexible material for defining the opening and allowing a user to vary its size. However, the structures and materials which provide these openings introduce a wide variety of complexities and disadvantages in these prior spirometers. These complexities make them susceptible to malfunctions and breakdowns and render them unreliable.

The spirometer of the present invention provides a construction which minimizes the expense of manufacture and assembly and gives precise, uniform and reliable performance. It comprises a small number of components which allow the user to measure breathing volume or flow rates of human subjects by taking pressure measurements over an extended range of breath flow rates. This spirometer includes a mouthpiece/transducer which is inexpensive and disposable and which does not require calibration.

SUMMARY OF THE INVENTION

In accordance with one embodiment of the present invention, a spirometer includes a portable housing which a user may easily hold in his or her hand. A hollow, elongate body releasably secured to the housing has a first opening through which a subject inhales or exhales, a second opening through which the subject's breath enters the elongate body when the subject inhales or discharges from the body when the subject exhales, and a third opening disposed between the first and second openings. The elongate body constricts the flow of breath at the second opening to develop measurable back pressure in the elongate body.

An electrical pressure transducer disposed in fluid communication with the third opening measures the pressure of the breath moving through the elongate body. The transducer provides signals to a central processing unit (CPU), including a keyboard and a display. These conventional data processing and control devices process the signals, and they store and display the data in a meaningful form.

As the flow rate through the second opening diminishes, the central processing unit permits a power source, e.g. a rechargeable battery pack disposed on the housing, to energize a solenoid secured to the housing. This solenoid includes a plunger which extends through the central bore of the solenoid and has a plug member fixedly secured at one end and a spring disposed around the opposite end between a stop on the plunger and the housing of the solenoid. The solenoid moves the plug member to a first position so that it may close a predetermined portion of the second opening to increase the back pressure in the elongate housing and allow the transducer to measure pressure at low flow rates. The spring returns the plug member out to a second position where it does not affect any portion of the second opening.

In operation, a subject breathes into the first opening of the elongate body; and his or her breath moves through the second opening and out of the housing. As the breath moves through the elongate body, the pressure transducer measures the pressure at predetermined time intervals. The transducer provides signals to the CPU which stores, processes, and transmits them to the display and/or to a printer.

When the subject's forced air flow diminishes to a predetermined level, as detected by the pressure transducer, the computer controls energize the solenoid which moves the obstruction plug member to partially close the second opening and allow the transducer to continue to measure pressure levels within its most accurate working pressure range. The spirometer operates similarly when the subject inhales through the first opening. Thus, the transducer provides accurate and consistent data.

BRIEF DESCRIPTION OF THE DRAWINGS

For a more complete understanding of this invention, one should now refer to the embodiment illustrated in greater detail in the accompanying drawings and described below by way of an example of the invention. In the drawings:

FIG. 1 is a perspective view of an embodiment of the spirometer of the present invention.

FIG. 2 is an exploded perspective view of the two halves of the spirometer housing.

While the drawings and the following text describe the invention in connection with one embodiment, one will understand that the invention is not limited to this embodiment. Furthermore, one should understand that the drawings are not necessarily to scale and that graphic symbols, diagrammatic representations and fragmentary views, in part, illustrate this embodiment. In certain instances, the drawings and the following text may not include details which are not necessary for an understanding of the present invention.

DETAILED DESCRIPTION OF THE DRAWINGS AND AN EMBODIMENT

Figure 3:
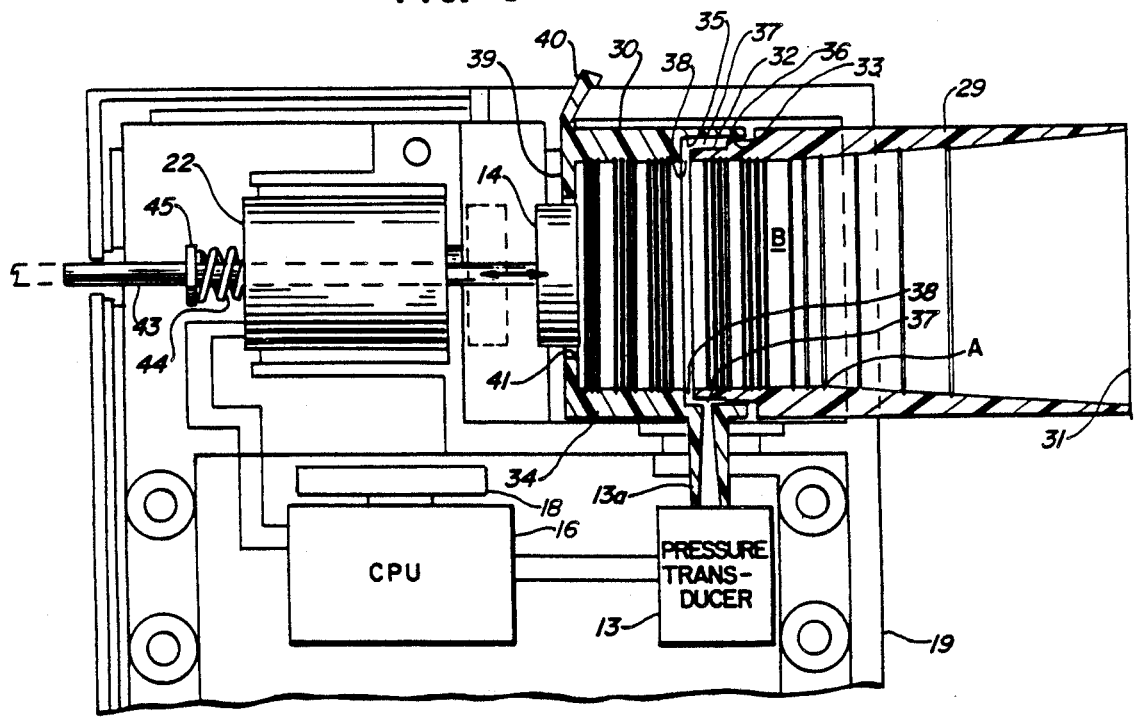
FIG. 3 is sectional view showing the elongate body through which a subject exhales or inhales and the plug member which closes a portion of the fluid constricting opening of the elongate body.

Turning now to the drawings, FIGS. 1-3 show an embodiment of the spirometer of the present invention at 10. The spirometer generally includes a housing 11 which a user may easily hold in his or her hand; a hollow, elongate body 12 through which a subject breathes; an electronic pressure transducer 13 (See FIG. 3) which measures the back pressure of the breath moving through the elongate body; a plug member 14; and computer controls 15 (See FIG. 3), including a central processing unit 16, a keyboard 17, and an LCD display 18, connected together electrically.

The housing 11 includes a back half segment 19 and a front half segment 20 (See FIG. 2) fixedly secured together to form the housing. The two segments are made out of plastic or any other material of high strength and rigidity. The half segment 19 includes projections 21a and 21b which define a seat for a solenoid 22 which moves the plug member 14 as described below. The half segment 19 also includes a pair of ribs 23a and 23b and a base plate 24 which, along with a second pair of ribs 25a and 25b and a second base plate 26 of the half segment 20, releasably secure the hollow, elongate body 12 to the housing 11. The half segments 19 and 20 receives the computer controls between them; and the half segment 20 includes a window 27 for the LCD display 18 and a seat 28 for the keyboard 17.

The hollow, elongate body 12 is also a plastic material or any material of high strength and rigidity. It includes a first segment 29 which is a round tube and a second segment 30. The first segment 29 defines a central bore with a first opening 31 at one end through which a human subject breathes. The diameter of the central bore decreases at a constant rate between the opening 31 and a point A (See FIG. 3) to minimize air resonance artifacts. From the point A to the second, opposite end of the first segment 29, the central bore has a constant diameter to facilitate laminar flow. At the second end, the first segment 29 defines a two-step annular seat, including a step 32 and step 33.

The second segment 30 includes a tube portion 34 which defines a central bore of constant diameter. The diameter of this bore equals the diameter of the bore section which has a constant diameter and which extends through the first segment 29. One end of the tube portion 34 includes an annular recess 35 which extends outward of the central bore of the tube portion. The tube portion's distal end 36 circumjacent the recess 35 engages the tube segment 29 at the step 33 in fluid-tight pressure contact to releasably secure the first segment 29 to the tube portion 34 of the second segment 30.

Connected together, the segments 29 and 30 define a central bore B for the elongate body 12, an annular space or opening 37 in the walls of the body 12, and an annular slit 38 which provides fluid communication between the opening 37 and the bore B where the bore has a constant diameter. The volume of opening 37 is sufficiently small to maximize the pressure sensitivity of the transducer 13. The slit has a width measured longitudinally of the bore B) which is sufficiently narrow to prevent turbulent flow in the opening 37 and establish stable pressures in the opening 37. By way of one specific example, a spirometer of small size and inexpensive construction was fabricated with the slit 38 of 0.005 inches.

The second segment 30 also includes a tube portion 13a which provides fluid communication between the space 37 and the pressure transducer 13. Thus, the pressure transducer 13 measures the pressure of the fluid flowing through the bore B at slit 38 where the configuration of the bore B, the slit 38 and the opening 37 stabilize disturbances, e.g. turbulent flow and venturi effect.

Finally, the second segment 30 includes a rectangular plate portion 39 which partially closes the bore B at the end of the second segment opposite the end which defines annular recess 35. The sides of this plate portion 39 extend beyond the tube portion 34 and into the space between the ribs 23a and 23b and between the ribs 25a and 25b of the housing 11 to releasably secure the elongate body 12 and the transducer 13 to the housing. It has a tab 40 which extends outward from its top end and allows a user of the spirometer to disconnect the elongate body 12 from the housing 11. To do this, the user pushes the tab 40 towards the solenoid 22 and moves the elongate body 12 outward of the housing 11.

The plate portion 39 defines a second, round opening 41 in the elongate body 12. (The slit 38 and the annular space 37 define a third opening in this body 12.) This second opening 41 allows breath to enter into the bore B and to discharge from it. Its diameter is substantially smaller than the first opening 31 so that the plate 39 may restrict the flow of the breath and stop sputum. The plug member 14, which is a thin disc made of plastic or any other suitable material, further restricts the flow of breath by closing a substantial portion of the second opening 41 when the flow of breath diminishes below a predetermined level.

Figure 4:
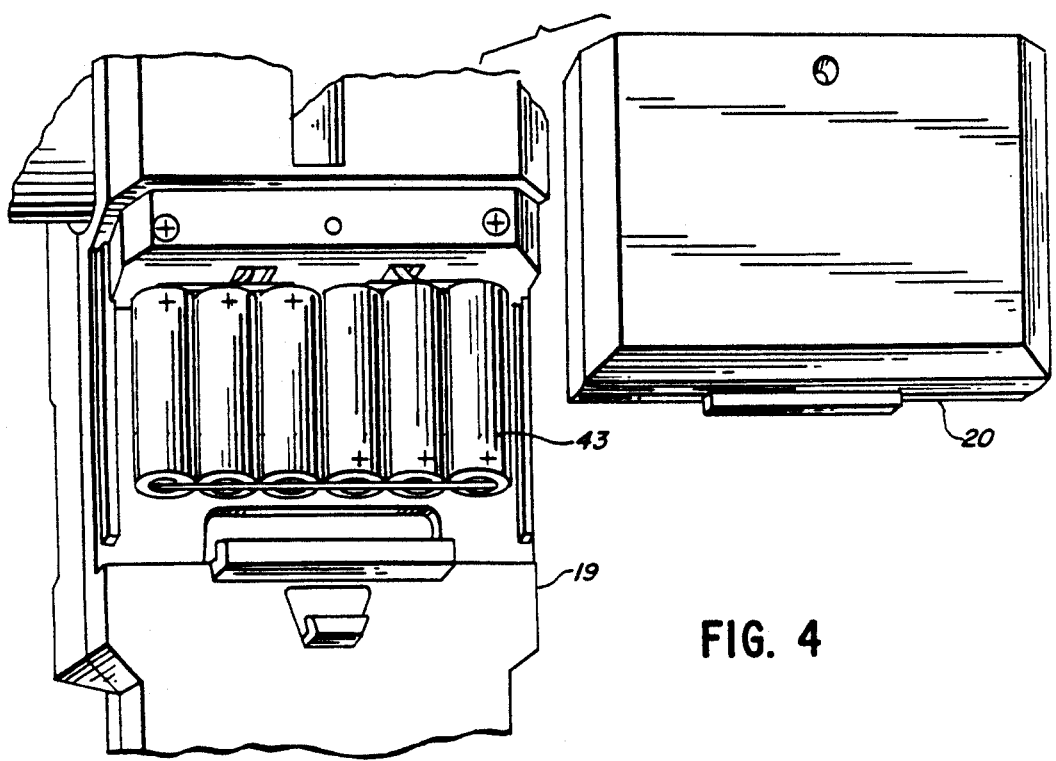
FIG. 4 is a partial perspective view of the rear portion of the spirometer housing, which supports a rechargeable battery pack.

When the flow rate reaches this level, as determined by the pressure transducer 13, the CPU 16 enables the spirometer's power source 2, e.g. a rechargeable battery pack, (See FIG. 4) to energize the solenoid 22. (Suitable electrical connections allow communication between the power source, transducer, CPU, and solenoid.) The solenoid 22 includes a plunger 43 which extends through the solenoid's central bore and which supports the plug member 14 at one end and a spring 44 at the opposite end. The spring 44, disposed between the solenoid housing and a stop 45 fixedly secured to the plunger 43, biases the plunger and this plug member 14 away from the second opening 41. (To the left in FIG. 3). The plug member 14 remains in this position (in phantom in FIG. 3) until the fluid pressure in the annular opening 37 diminishes below the predetermined level, e.g. a pressure equivalent to a flow of 3.0 liters per second.

At this point, the CPU allows the power source 42 to energize the solenoid; and the solenoid's coil produces a flux within its core which moves the plunger 43 towards the elongate body 12 and the plug member 14 in the second opening 41. Thus, the plug member 14 moves to the position shown in solid lines in FIG. 3. The controls then continue to energize the solenoid and maintain the plug member 14 in this location until the end of the testing procedure or until the transducer senses a pressure greater than the predetermined pressure identified above.

In operation, a subject breathes into (exhales) the first opening 31 of the elongate body 12; and his or her breath moves through the second opening 41 and out of the housing 11. As the breath moves through the elongate body 12, the pressure transducer 13 measures the pressure at predetermined sampling and storage intervals. When the subject's forced air flow diminishes to a predetermined level, the computer controls allow the power source 42 to energize the solenoid 22 which moves the obstruction plug member 14 into the second opening 41. Thus, the spirometer utilizes the most accurate working pressure range of the pressure transducer to provide accurate and consistent data. The spirometer operates similarly when a subject inhales through the first opening and the fluid flow reverses direction.

The pressure transducer provides data which the CPU receives and converts into a series of flow and time points for each pulmonary test. The CPU temporarily stores the data and establishes an optimum scaling factor to provide the best resolution of these data points. It then applies an algorithm, e.g. the cubic algorithm of least squares, to the data to determine the instantaneous flow about a point in time. Then, it transmits the data to the spirometer display.

While the above text and the drawings disclose one embodiment, one will understand, of course, that the invention is not limited to this embodiment. Those skilled in the art to which the invention pertains may make modifications and other embodiments employing the principals of this invention, particularly upon considering the foregoing teachings. For example, one skilled in the art may make the configuration of the plug member and the first and second openings a non-circular configuration. Therefore, by the appended claims, the applicants intend to cover any such modifications and other embodiments as incorporate those features which constitute the essential features of this invention.

What is claimed is:

1. A spirometer for measuring breathing functions of a human subject, said spirometer comprising: a hollow elongate body with a first opening through which the subject inhales or exhales, a second opening through which the breath enters the elongate body when the subject inhales or discharges from the body when the subject exhales, and a third opening disposed between said first and second openings; pressure sensing means in fluid communication with said third opening of said elongate body for sensing the pressure of the breath moving through said hollow elongate body; plug means disposed proximate said second opening of said elongate body for closing a predetermined portion of said second opening for levels of breath flow rate below a predetermined level without stopping the flow of breath through said body, said plug means allowing free, unobstructed fluid flow through the second opening for levels of breath flow rate above the predetermined level.

2. The spirometer of claim 1 further comprising a control means for receiving signals from said pressure sensing means and providing signals to said plug means; and connecting means for connecting the pressure sensing means and the plug means to the control means; said plug means partially closing and opening said portion of said second opening in response to the signals provided by said control means.

3. The spirometer of claim 1 wherein said elongate body is a round tubular member and said third opening includes an annular opening portion which lies between the outside surface and the inside surface of the body and extends circumstantially around the body and an annular slit portion which extends radially and circumferentially of the body between the annular opening portion and the hollow of the body, said slit portion providing fluid communication between the annular opening portion and the hollow inside of the elongate body.

4. The spirometer of claim 1, wherein said plug means includes a plug member, a spring, and a solenoid for moving said plug member between a first predetermined position away from said second opening and a second predetermined position in which said plug member closes said predetermined portion of said second opening.

5. The spirometer of claim 1 further comprising a housing for containing said pressure sensing means and said plug means, said elongate body extending into said housing and being releasably secured to said housing.

6. The spirometer of claim 1 wherein said elongate body is a round tube with said first opening disposed at one end and said second opening at the opposite end.

7. The spirometer of claim 1, wherein said pressure sensing means includes an electric transducer.

8. A spirometer for measuring breathing functions of a human subject, said spirometer comprising: a housing; a hollow elongate body releasably secured to said housing, said elongate body including a first opening through which the subject inhales or exhales, a second opening through which the breath enters the elongate body when the subject inhales or discharges from the body when the subject exhales, and a third opening disposed between said first and second opening; electronic pressure sensing means in fluid communication with said third opening of said elongate body for sensing the pressure of the breath moving through said hollow elongate body; a plug member disposed proximate said elongate body for closing a predetermined portion of said second opening; driving means disposed in said housing for moving said plug member between a first predetermined position away from said second opening where the plug member does not obstruct fluid flow through the second opening and a second predetermined position in which the plug member closes a predetermined portion of said second opening; control means disposed in said housing for receiving signals from said electronic pressure sensing means and providing signals to said driving means to activate the driving means, said driving means moving said plug member to the second position for levels of breath flow rate below a predetermined level and to the first position for levels of breath flow rate above the predetermined level in response to the signals provided by said control means.

* * * * *

UNITED STATES PATENT AND TRADEMARK OFFICE
CERTIFICATE OF CORRECTION

PATENT NO. : 4,991,591

DATED : February 12, 1991

INVENTOR(S) : William C. Jones and William C. Jones, Jr.

It is certified that error appears in the above-identified patent and that said Letters Patent is hereby corrected as shown below:

Column 6, line 15, delete "circumstantially" and substitute therefor -- circumferentially --.

Signed and Sealed this

Eleventh Day of August, 1992

Attest:

DOUGLAS B. COMER

*Attesting Officer*      Acting Commissioner of Patents and Trademarks